United States Patent [19]

Jørgensen et al.

[11] 4,424,229

[45] Jan. 3, 1984

[54] FLUORINE CONTAINING 2,4,5-TRIPHENYLIMIDAZOLES

[75] Inventors: Dan Jørgensen, Vedbaek; Hjarne Dyrsting, Virum, both of Denmark

[73] Assignee: A/S Dumex (Dumex Ltd.), Copenhagen, Denmark

[21] Appl. No.: 356,643

[22] Filed: Mar. 10, 1982

Related U.S. Application Data

[63] Continuation-in-part of Ser. No. 32,691, Apr. 23, 1979, abandoned.

[51] Int. Cl.$^3$ .................. A61K 31/415; C07D 233/56
[52] U.S. Cl. .................................. 424/273 R; 548/346
[58] Field of Search ................. 548/337, 346; 424/273

[56] References Cited

U.S. PATENT DOCUMENTS 3,707,475  12/1972  Lombardino et al. .............. 548/346

3,784,557  1/1974  Cescon ............................... 548/346

OTHER PUBLICATIONS

Lombardino et al., Journ. Med. Chem. 1974, vol. 17, No. 11, pp. 1182–1188.

Primary Examiner—Ethel G. Love
Attorney, Agent, or Firm—Wenderoth, Lind & Ponack

[57] ABSTRACT

Fluorosubstituted benzaldehydes are condensed with anisil and ammonium acetate to yield the corresponding 2-(fluorosubstituted phenyl)-4,5-bis(4-methoxyphenyl)imidazoles. Alternatively fluorosubstituted benzaldehydes are condensed with anisil monoxime and ammonium acetate to yield the corresponding 2-(fluorosubstituted phenyl)-4,5-bis(4-methoxyphenyl)-imidazole-3-oxides which can subsequently be reduced to yield the corresponding 2-(fluorosubstituted phenyl)-4,5-bis(4-methoxyphenyl)imidazoles. These imidazoles have interesting pharmacological properties.

2 Claims, No Drawings

FLUORINE CONTAINING 2,4,5-TRIPHENYLIMIDAZOLES

This application is a continuation-in-part of application Ser. No. 32,691, filed Apr. 23, 1979 (now abandoned).

The present invention relates to novel imidazole derivatives and to processes for their preparation. The novel compounds possess interesting pharmacological properties.

Certain substituted imidazoles have been described in the literature and these have been prepared in a number of different ways and for various purposes.

In Davidson, Weiss and Jelling: J. Org. Chem 2, 319 (1937); Brederech and Theilig: Chem. Ber. 86, 88 (1953); Brederech, Gompper and Hayer: Chem. Ber. 92, 338 (1959); White and Sonnenberg: J. Org. Chem. 29, 1926 (1964); Ogata, Kawasaki and Sugiura: J. Org. Chem. 34, 3981 (1969); H. Lettau: Z. Chem. 11, 10 (1971) and Wegner and Schunack: Arch. Pharmaz. 307, 492 (1974) various imidazoles are prepared without any indication as to their utility.

Radziszewski: Chem. Ber. 10, 70 (1877), Cook and Jones: J. Chem. Soc. 278 (1941) and others have found that a number of arylimidazoles exhibit chemiluminescence under certain conditions. This property can be utilized in certain copying techniques (e.g. xerography) and forms the basis of German Pat. No. 1,106,599, Belgian Pat. No. 585,555 and French Pat. No. 1,351,818.

Certain 2,4,5-triarylimidazoles have been tested as anti-fertility agents by Bhaduri and Khanna: Indian J. Chem. 4, 419 (1966).

Certain 2-alkyl-4,5-diarylimidazles are described in German Offenlegungsschrift No. 2,064,520 as possessing analgesic, antiinflammatory and antipyretic activity. One of the preferred compounds of this series, 2-isopropyl-4,5-bis(4-methoxyphenyl)imidazole, has been included in the pharmacological tests described hereinafter, from which it can be seen that this preferred compound possesses a much weaker analgesic activity than the compounds of the present invention.

Certain 2,4,5-trisubstituted imidazoles containing a trifluoromethyl group in one of these positions and in some cases also substituted in the 1-position have been described in German Offenlegungsschrift No. 2,155,558 (cf. Lombardino and Wieseman: J. Med. Chem. 17, 1182 (1974)). The preferred compound of this series, 2-trifluoromethyl-4,5-bis(4-methoxyphenyl)imidazole, has been included in the pharmacological data hereinafter described from which it will be seen that tests indicate this preferred compound to possess a weaker analgesic activity, but a higher toxicity than the compounds of the present invention.

Our British Pat. No. 1,469,532 describes and claims certain imidazoles substituted in the 1-position by an acetic acid or propionic acid group or ester thereof. Our investigations on animal models conventionally employed in pharmacology using such compounds show that in general, arylimidazoles substituted in the 1-position by a propionic acid group are more active than the corresponding imidazole unsubstituted in the 1-position.

The present invention is based on the discovery of certain 2-(fluoro-substituted phenyl)-4,5-bis(4-methoxyphenyl)imidazoles unsubstituted in the 1-position which possess substantially improved properties over the compounds disclosed in German Offenlegungsschrift Nos. 2,064,520 and 2,155,558 and more particularly show improved activity over 1-(2-carboxyethyl)-2-(4-fluorophenyl)-4,5-bis(4-methoxyphenyl)imidazole, a corresponding imidazole substituted in the 1-position by a propionic acid group.

Thus according to the present invention there are provided compounds of the formula:

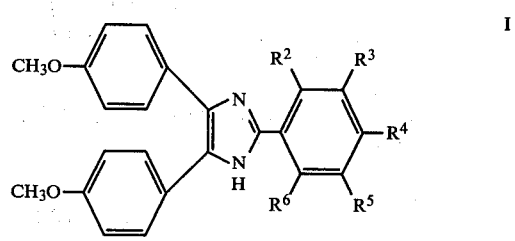

wherein one or two of the substituents $R^2$, $R^3$, $R^4$, $R^5$ and $R^6$ represent a fluorine atom while the remaining substituents are hydrogen atoms.

The compounds according to the present invention are:
2-(2-Fluorphenyl)-4,5-bis(4-methoxyphenyl)imidazole
2-(3-Fluorphenyl)-4,5-bis(4-methoxyphenyl)imidazole
2-(4-Fluorphenyl)-4,5-bis(4-methoxyphenyl)imidazole
2-(2,3-Difluorphenyl)-4,5-bis(4-methoxyphenyl)imidazole
2-(2,4-Difluorphenyl)-4,5-bis(4-methoxyphenyl)imidazole
2-(2,5-Difluorphenyl)-4,5-bis(4-methoxyphenyl)imidazole
2-(2,6-Difluorphenyl)-4,5-bis(4-methoxyphenyl)imidazole
2-(3,4-Difluorphenyl)-4,5-bis(4-methoxyphenyl)imidazole
2-(3,5-Difluorphenyl)-4,5-bis(4-methoxyphenyl)imidazole Tests which we have conducted show the compounds of the invention are potent prostaglandin synthesis inhibitors both in vitro and in vivo and possess interesting pharmacological properties. In particular the compounds of the invention exhibit good analgesic, antiinflammatory and antipyretic activity whilst possessing low ulcerogenicity and toxicity.

A further very interesting property of the compounds of the invention is their ability to inhibit arachidonic acid induced bronchoconstrictions in guinea-pigs, a property which can be utilized in the treatment of astmatic diseases. This property has not earlier been described with compounds of closely related structure.

The compounds of the present invention were submitted to a pharmacological screening program comprising the following tests:

Tests for analgesic activity

1. Writhing test in mice. (SPF females of the strain NMRI/BOM, weighing 20–25 g). The test substance was administered by gavage ½ hour prior to an intraperitoneal injection of acetic acid. The number of writhing movements in 20 minutes was counted.

2. Randall-Selitto test in rats. (SPF males of the strain Sprague-Dawley, weighing 90–100 g). The test was performed on the whole as described by Randall and Selitto: Arch. Int. Pharmacodyn. Ther. 111, 409 (1957). An analgesia-meter of the make Ugo Basile was used and the test substance was administered by gavage 2 hours after injection of a suspension of brewer's yeast into the rat paw.

Test for antiinflammatory activity in rats

SPF males of the strain Sprague-Dawley, weighing ~150 g were used. The test was performed according to Winter et al.: Proc. Soc. Exp. Biol. Med. 111, 544 (1962). The test substance was given by gavage 1 hour prior to injection of a carrageenin-suspension into the rat paw.

Test for acute toxicity ($LD_{50}$) in mice

The test substance was administered by gavage. Observation period: 168 hours

Ulcerogenic activity in rats

SPF males of the strain Sprague-Dawley weighing 180–250 g were used. 5 hours after administration by gavage of the test substance the rates were killed by an overdose of ether. The stomachs were removed and opened along the greater curvature. The number of ulcers was assessed and compared to control rats.

Prostaglandin-synthetase inhibition test

Performed on the whole according to Vane: Nature New Biol. 231, 232 (1972).

Platelet aggregation inhibition test

The ability of the test substance to inhibit arachidonic acid induced aggregation of human platelet rich plasma was tested in a HU aggregometer (from H. Upchurch & Co. Ltd.). Inhibition of arachidonic acid (AA) induced bronchoconstrictions in guinea-pigs.

Test compounds were given intravenously to anesthetized guinea-pigs 5 min. before intravenous injection of AA (20–500 μg/kg). Bronchial pressure was measured and percent inhibition calculated as compared to the mean of 3 preceding AA-induced control constrictions obtained after injection of vehicle in the same animal. $ID_{50}$-values (doses inhibiting control constrictions by 50%) were calculated by means of regression analysis.

Table 1 and 2 comprise the results of the pharmacological screening of the following compounds:

| Compound No. | |
|---|---|
| 1. | 1-(2-Carboxyethyl)-2-(4-fluorphenyl)-4,5-bis(4-methoxyphenyl)imidazole. |

-continued

| Compound No. | |
|---|---|
| 2. | 2-(2-Fluorphenyl)-4,5-bis(4-methoxyphenyl)imidazole. |
| 3. | 2-(3-Fluorphenyl)-4,5-bis(4-methoxyphenyl)imidazole. |
| 4. | 2-(4-Fluorphenyl)-4,5-bis(4-methoxyphenyl)imidazole. |
| 5. | 2-(2,3-Difluorphenyl)-4,5-bis(4-methoxyphenyl)imidazole. |
| 6. | 2-(2,4-Difluorphenyl)-4,5-bis(4-methoxyphenyl)imidazole. |
| 7. | 2-(2,5-Difluorphenyl)-4,5-bis(4-methoxyphenyl)imidazole. |
| 8. | 2-(2,6-Difluorphenyl)-4,5-bis(4-methoxyphenyl)imidazole. |
| 9. | 2-(3,4-Difluorphenyl)-4,5-bis(4-methoxyphenyl)imidazole. |
| 10. | 2-(3,5-Difluorphenyl)-4,5-bis(4-methoxyphenyl)imidazole. |
| 11. | 2-Trifluormethyl-4,5-bis(4-methoxyphenyl)imidazole. |
| 12. | 2-Isopropyl-4,5-bis(4-methoxyphenyl)imidazole. |
| 13. | Indomethacin.[1] |
| 14. | Naproxen.[1] |
| 15. | Acetyl salicylic acid.[1] |
| 16. | Salbutamol.[2] |

[1]Generally acknowledged anti-inflammatory compounds.
[2]A $\beta_2$-receptor stimulator, used for the treatment of astmatic diseases.

TABLE 1

The doses stated for $ED_{50}$ and $LD_{50}$ are mg/kg

| Compound No. | Analgesic $ED_{50}$ Writhing test | Analgesia-meter | Antiinflammatory test $ED_{50}$ | Acute toxicity $LD_{50}$ | Ulcerogenic activity $ED_{50}$ | Inhibition of PG-synthetase $IC_{50}$ μg/10 μg AA+ | Inhibition of platelet aggregation $IC_{100}$ μg/190 μg AA+ |
|---|---|---|---|---|---|---|---|
| 1 | >200 | | | >2000 | | | |
| 2 | 15 | 0.3 | 130 | >2000 | 590 | 0.23 | 0.024 |
| 3 | 3.2 | 0.25 | 38 | >2000 | 870 | 0.21 | 0.12 |
| 4 | 5 | 0.3 | 14 | 1900 | 360 | 0.18 | 0.048 |
| 5 | 4.6 | 0.55 | 120 | 3125 | 800 | 0.21 | 0.024 |
| 6 | 4 | 0.8 | 47 | >2000 | 1580 | 0.27 | 0.12 |
| 7 | 16 | 0.55 | 110 | >2000 | 1000 | 1.71 | 0.024 |
| 8 | 6.8 | 0.55 | 300 | >2000 | >300 | 0.13 | 0.012 |
| 9 | 1.9 | 0.062 | 15 | >2000 | 45 | 0.11 | 0.006 |
| 10 | 10 | 0.45 | 150 | >2000 | 780 | 0.38 | 0.12 |
| 11 | 75 | | 25 | >2000 | 450 | | 0.06 |
| 12 | 200 | | | >2000 | | | |
| 13 | 8 | 0.36 | 28 | 21 | 9.7 | 0.65 | 1.19 |
| 14 | 33 | 1.6 | 10 | 1340 | 19.5 | 0.49 | 4.76 |
| 15 | 100 | | 350 | 1700 | 340 | 7.61 | 2.38 |

AA+ = Arachidonic acid

TABLE 2

Inhibition of arachidonic acid induced bronchoconstrictions in guinea-pigs.

| Compound No. | Number of guinea-pigs | $ID_{50}$ μg/kg |
|---|---|---|
| 2 | 3 | 10.6 |
| 3 | 7 | 3.6 |
| 4 | 5 | 4.7 |
| 5 | 3 | 8.7 |
| 6 | 14 | 2.1 |
| 7 | 4 | 2.4 |
| 8 | 3 | 4.9 |
| 9 | 4 | 11.5 |
| 10 | 3 | 9.7 |
| 13 | 13 | 115 |
| 15 | 3 | 234 |
| 16 | 3 | 16 |

The compounds of the present invention may be prepared by the following processes:

(a) the reaction of anisil and ammonium acetate with a compound of the formula:

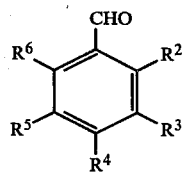

where one or two of the substituents $R^2$, $R^3$, $R^4$, $R^5$ and $R^6$ represent a fluorine atom, while the remaining substituents represent hydrogen atoms, whereby a compound of formula I as hereinbefore defined is obtained.

The reaction may, for example, be effected in a manner analogous to the method of White and Sonnenberg: J. Org. Chem. 29, 1926 (1964). Thus anisil, ammonium acetate and the appropriate aldehyde are reacted together conveniently in the presence of a protic solvent, preferably acetic acid.

It is convenient to use the anisil and aldehyde in equimolar quantities in which case it is advantageous to use about five times the equimolar amount of ammonium acetate. It is convenient to use about 2 liters of solvent e.g. acetic acid per mole of anisil. The reaction is conveniently effected at the reflux temperature of the reaction mixture, but lower temperatures will also lead to the desired product. The precise proportion between the reactants, the concentration of each reactant and the reaction temperature is not of vital importance.

(b) the reduction of a compound of the formula:

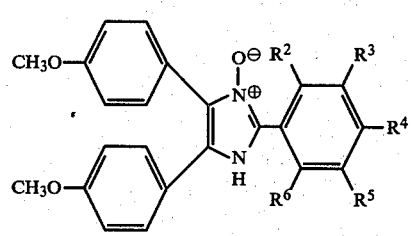

where $R^2$, $R^3$, $R^4$, $R^5$ and $R^6$ are as hereinbefore defined, whereby a compound of formula I as hereinbefore defined is obtained.

The reduction is advantageously effected in the presence of zinc, preferably in powder form, and is conveniently effected at the reflux temperature of the reaction mixture.

The compound of formula III is preferably first prepared by reacting anisil monoxime with ammonium acetate and a compound of formula II as hereinbefore defined.

The reaction and reduction may, for example, be effected in a manner analogous to the method of, H. Lettau: Z. Chem. 11, 10 (1971). Thus anisil monoxime, ammonium acetate and the appropriate aldehyde are reacted together advantageously in the presence of a lower alkanoic acid, e.g. acetic acid, and the 3-oxide thus obtained is reduced, preferably in situ i.e. without isolation, conveniently by the addition of zinc preferably in the form of a powder. It is convenient to use the anisil monoxime and aldehyde in equimolar quantities in which case it is advantageous to use about five times the equimolar amount of ammonium acetate. The amount of solvent used is conveniently 2 liters per mole of anisil monoxime. The reaction is preferably effected at the reflux temperature of the reaction mixture.

According to a still further feature of the present invention there are provided pharmaceutical or veterinary compositions for the treatment of human patients or domestic mammals, comprising as active ingredient at least one compound of formula I as hereinbefore defined in association with a pharmaceutical or veterinary carrier or excipient.

The compositions may be presented in a form suitable for oral, topical, rectal or parenteral administration or in a form for inhalation. Thus, for example, the compositions may be solid or liquid and may take the form of granules, tablets, coated tablets, capsules, syrups, suppositories, ointments, creams, emulsions, suspensions, drops or injectable solutions, such compositions comprising carriers or excipients conventionally used in the pharmaceutical and veterinary art.

Advantageously, the compositions may be formulated as dosage units, each unit being adapted to supply a fixed dose of active ingredient. Tablets, coated tablets and capsules are examples of suitable dosage unit forms. Each dosage unit preferably contains 10 to 500 mg of active ingredient. The total daily dosage is 2–5 mg/kg body weight.

The following Examples illustrate the preparation of compounds according to the invention:

EXAMPLE 1

2-(4-Fluorophenyl)-4,5-bis(4-methoxyphenyl)imidazole 800 ml of acetic acid, 310 g (4.0 mole) of ammonium acetate, 108 g (0.4 mole) of anisil and 50 g (0.4 mole) of 4-fluorobenzaldehyde are refluxed together for one hour. Boiling water is then added to the clear solution until a slight turbidity persists and the heating is stopped. After cooling the white precipitate formed is filtered off, washed with 2 N ammonia and then with water, dried and recrystallised from 2-propanol.

Yield of recrystallised product: 119.7 g (80%) The product is homogeneous by TLC and shows a melting point of 207.5°–210.5° C.

|  |  | C | H | N |
|---|---|---|---|---|
| $C_{23}H_{19}FN_2O_2$ | Calc. | 74.28 | 5.15 | 7.53 |
| (374.40) | Found | 73.95 | 4.91 | 7.51 |

The mass spectrum shows a molecular ion at $m/e=374$ (base peak), $m/e=359$ (M-15), metastable $m/e=345$ (corresponding to the fragmentation $M^+\rightarrow(M-15)^+$).

The IR-spectrum shows the following characteristics: 3450 cm$^{-1}$ (broad) NH; 3100–2900 cm$^{-1}$ NH and CH (aromatic); 2840 cm$^{-1}$ CH (OCH$_3$) 1620, 1525, 1505 cm$^{-1}$ aromatic ring system; 1250, 1035 cm$^{-1}$ aryl-OCH$_3$; 385 cm$^{-1}$ 1,4-substituted benzene rings.

The NMR-spectrum shows the following characteristics:

$\delta$(ppm) = 3.87, singlet (6H) (CH$_3$O) × 2
7.0; 7.6, AB quartet (8H) (C$_6$H$_4$OCH$_3$) × 2
7.1, triplet (2H) ⎫
7.9, doublet of doublets (2H) ⎬ (C$_6$H$_4$F)
~10.5, broad singlet (1H) (NH) ⎭

EXAMPLE 2

2-(2,4-Difluorophenyl)-4,5-bis(4-methoxyphenyl)imidazole 210 ml of acetic acid, 84 g (1.09 mole) of ammonium acetate, 28.4 g (0.105 mole) of anisil and 14.95 g (0.105 mole) of 2,4-difluorobenzaldehyde are refluxed together for one hour. The heating is stopped and boiling water is added to the clear solution until a slight turbidity persists.

After cooling the white precipitate formed is filtered off, washed with 2 N ammonia and then with water, dried and recrystallised from 2-propanol.

Yield of recrystallised product: 34.9 g (85%). The product is homogenous by TLC and shows a melting point of 137°–8° C.

|  |  | C | H | N |
|---|---|---|---|---|
| $C_{23}H_{18}F_2N_2O_2$ | Calc. | 70.38 | 4.62 | 7.18 |
| (392.39) | Found | 70.45 | 4.50 | 7.11 |

The mass sprectrum shows a molecular ion at m/e=392 (base peak), m/e=377 (M-15), metastable m/e=363 (corresponding to the fragmentation $M^+ \rightarrow (M-15)^+$).

The IR-spectrum shows the following characteristics: 3470 cm$^{-1}$ (sharp) NH; 3500–3400 cm$^{-1}$ (broad) NH; 3100–3000 cm$^{-1}$ CH (aromatic); 2845 cm$^{-1}$ CH (OCH$_3$); 1620, 1525, 1500 cm$^{-1}$ aromatic ring system; 1250, 1035 cm$^{-1}$ aryl-O-CH$_3$; 855, 845, 835 cm$^{-1}$ 1,4-substituted benzene rings.

The NMR-spectrum shows the following characteristics:

δ(ppm) = 3.82, singlet (6H) (CH$_3$O) × 2
6.9; 7.5, AB quartlet (8H) (C$_6$H$_4$OCH$_3$) × 2
6.9, multiplets (2H)  ⎫
8.4, multiplet (1H)       ⎬ (C$_6$H$_3$F$_2$)
9.5, broad singlet (1H) (NH)

2,4-Difluorobenzaldehyde can be prepared from 2,4-difluorotoluene according to Gunther Lock: Montash. 90, 680 (1959).

EXAMPLE 3

2-(4-Fluorophenyl)-4,5-bis(4-methoxyphenyl)imidazole 28.5 g (0.1 mole) of anisil monoxime, 20 g (0.26 mole) of ammonium acetate, 12.4 g (0.1 mole) of 4-fluorobenzaldehyde and 200 ml of acetic acid are refluxed together. After 2 hours, 20 g of zinc powder are added to the reaction mixture in small portions, and the refluxing is continued for a further 4 hours. After cooling, the precipitate of zinc acetate and unreacted zinc powder is filtered off and discarded. The filtrate is added dropwise to one liter of water with vigorous stirring. The precipitate formed is filtered off, washed by suspension first in 2 N ammonia and then in water, dried and finally recrystallised from 2-propanol Yield of Recrystallised product: 29 g (74%)
Melting point: 208°–210° C.
IR spectrum identical with the IR-spectrum of the product from Example 1.

EXAMPLE 4

2-(2,4-Difluorophenyl)-4,5-bis(4-methoxyphenyl)imidazole 28.5 g (0.1 mole) of anisil monoxime, 20 g (0.26 mole) of ammonium acetate, 14.2 g (0.1 mole) of 2,4-difluorobenzaldehyde and 200 ml of acetic acid are refluxed together. After 2 hours, 20 g of zinc powder are added to the reaction mixture in small portions, and the refluxing is continued for a further 4 hours. After cooling the precipitate of zinc acetate and unreacted zinc powder is filtered off and discarded. The filtrate is added dropwise to one liter of water under vigorous stirring. The precipitate formed is filtered off, washed by suspension first in 2 N ammonia and then in water, dried and finally recrystallised from 2-propanol.

Yield of recrystallised product: 32.3 g (82%).
Melting point: 137°–8° C.
IR-spectrum identical with the IR-spectrum of the product from Example 2.

EXAMPLE 5

2-(3-Fluorophenyl)-4,5-bis(4-methoxyphenyl)imidazole 380 ml of acetic acid, 151 g (1.96 mole) of ammonium acetate, 51 g (0.19 mole) of anisil and 23.5 g (0.189 mole) of 3-fluorobenzaldehyde are refluxed together for one hour. Boiling water is then added to the clear solution until a slight turbidity persists and the heating is stopped. After cooling the white precipitate formed is filtered off, washed with 2 N ammonia and then with water, dried and recrystallised from 2-propanol.

Yield of recrystallised product: 40.5 g (57%).
The product is homogenous by TLC and shows a melting point of 221.7-223.7° C.

The IR-spectrum (KBr) shows the following characteristics: 3440 cm$^{-1}$ (broad) NH; 3100–2900 cm$^{-1}$ NH and CH (aromatic); 2840 cm$^{-1}$ CH (OCH$_3$); 1620, 1525 and 1495 cm$^{-1}$ aromatic ring system; 1250 and 1035 cm$^{-1}$ aryl-OCH$_3$; 835 cm$^{-1}$ 1,4-substituted benzene rings.

The 60 MHz $^1$H NMR-spectrum of a 10% solution in DMSO-d$_6$ shows the following characteristics:

δ(ppm) = 3.85 singlet (3H) (CH$_3$O)
3.90 singlet (3H) (CH$_3$O)
7.1; 7.7 AB quartet (8H) (C$_6$H$_4$OCH$_3$) × 2
~7.3 (pattern not resolved) (1H)  ⎫
~7.8 (pattern not resolved) (1H)  ⎬ (C$_6$H$_4$F)
8.1 multiplet (2H)                ⎭
13.1 broad singlet (1H) (NH)

EXAMPLE 6

2-(2-Fluorophenyl)-4,5-bis(4-methoxyphenyl)imidazole 380 ml of acetic acid, 151 g (1.96 mole) of ammonium acetate, 51 g (0.19 mole) of anisil and 23.5 g (0.189 mole) of 2-fluorobenzaldehyde are refluxed together for one hour. Boiling water is then added to the clear solution until a slight turbidity persists and the heating is stopped. After cooling the white precipitate formed is filtered off, washed with 2 N ammonia and then with water, dried and recrystallised from 2-propanol.

Yield of recrystallised product: 46.0 g (65%).
The product is homogenous by TLC and shows a melting point of 97.2°–104.4° C.

The IR-spectrum shows the following characteristics: 3460 cm$^{-1}$ (broad) NH; 3100–2900 cm$^{-1}$ NH and CH (aromatic); 2845 cm$^{-1}$ CH (OCH$_3$); 1620, 1525 and 1500 cm$^{-1}$ aromatic ring system; 1250 cm$^{-1}$ and 1035 cm$^{-1}$ aryl-OCH$_3$; 840 cm$^{-1}$ 1,4-substituted benzene rings.

The 60 MHz $^1$H NMR-spectrum of a 10% solution in DMSO-d$_6$ shows the following characteristics:

| δ(ppm) = | 3.80 singlet (3H) (CH$_3$O) |
|---|---|
| | 3.85 singlet (3H) (CH$_3$O) |
| | 7.1; 7.6 AB quartet (8H) (C$_6$H$_4$OCH$_3$) × 2 |
| | ~7.3 (pattern not resolved) (2H) ⎫ |
| | ~7.5 (pattern not resolved) (1H) ⎬ (C$_6$H$_4$F) |
| | 8.2 doublet of doublets (1H) ⎭ |
| | 12.8 broad singlet (1H) (NH) |

EXAMPLE 7

2-(2,5-Difluorophenyl)-4,5-bis(4-methoxyphenyl)imidazole 200 ml of acetic acid, 77 g (1.0 mole) of ammonium acetate, 27 g (0.1 mole) of anisil and 14.95 g (0.105 mole) of 2,5-difluorobenzaldehyde are refluxed together for one hour. Boiling water is then added to th clear solution until a slight turbidity persists and the heating is stopped. After cooling the white precipitate formed is filtered off, washed with 2 N ammonia and then with water, dried and recrystallised from 2-propanol.

Yield of recrystallised product: 28.2 g (69%).

The product of homogenous by TLC and shows a melting point of 140.1°–141.6° C.

The IR-spectrum (KBr) shows the following characteristics: 3460 cm$^{-1}$ (broad) NH; 3100–2900 cm$^{-1}$ NH and CH (aromatic); 2850 cm$^{-1}$ CH (OCH$_3$); 1622, 1525 and 1500 cm$^{-1}$ aromatic ring systems; 1250 cm$^{-1}$ (assym.) and 1035 cm$^{-1}$ (sym.) C-O-C; 838 cm$^{-1}$ 1,4-disubstituted benzene rings.

The 60 MHz $^1$H NMR-spectrum of a 10% solution in DMSO-d$_6$ shows the following charactertistics:

| δ(ppm) = | 3.90 singlet (6H) (CH$_3$O) × 2 |
|---|---|
| | 7.3; 7.9 AB quartet (8H) (C$_6$H$_4$OCH$_3$) × 2 |
| | 7.6 multiplet (2H) ⎫ |
| | ⎬ (C$_6$H$_3$F$_2$) |
| | 8.2 multiplet (1H) ⎭ |
| | 13.1 broad singlet (1H) (NH) |

The 2,5-difluorobenzaldehyde used as a starting compound can be prepared from 1,4-difluorobenzene in the same way as described for 2,6-difluorobenzaldehyde by A. M. Roe et al.: J.Med. Chem. 11 (1968) 814. b$_{15}$=54°–56° C.

EXAMPLE 8

2-(2,6-Difluorophenyl)-4,5-bis(4-methoxyphenyl)imidazole 200 ml of acetic acid, 77 g (1.0 mole) of ammonium acetate, 27 g (0.1 mole) of anisil and 14.95 g (b 0.105 mole) of 2,6-difluorobenzaldehyde are refluxed together for one hour. Boiling water is then added to the clear solution until a slight turbidity persists and the heating is stopped. After cooling the white precipitate formed is filtered off, washed with 2 N ammonia and then with water, dried and recrystallised from 2-propanol/diisopropylether (1/1).

Yield of recrystallised product: 16.7 g (42%).

The product is homogenous by TLC and shows a melting point of 156.4°–157.4° C.

The IR-spectrum (KBr) shows the following characteristics: 3460 cm$^{-1}$ (broad) NH; 3140–2900 cm$^{-1}$ CH (aromatic); 2845 cm$^{-1}$ CH (OCH$_3$); 1620, 1525 and 1500 cm$^{-1}$ aromatic ring systems; 1250 cm$^{-1}$ (assym.) and 1035 cm$^{-1}$ (sym.) C-O-C; 850 and 840 cm$^{-1}$ 1,4-disubstituted benzene rings.

The 60 MHz $^1$H NMR-spectrum of a 10% solution in DMSO-d$_6$ shows the following characteristics:

| δ(ppm) = | 3.83 singlet (3H) (CH$_3$O) |
|---|---|
| | 3.80 singlet (3H) (CH$_3$O) |
| | 7.0; 7.5 AB quartet (4H) (C$_6$H$_4$OCH$_3$) |
| | 7.1; 7.6 AB quartet (4H) (C$_6$H$_4$OCH$_3$) |
| | ~7.2 hidden signal (1H) (C$_6$H$_3$F$_2$) |
| | 7.45 triplet (2H) (C$_6$H$_3$F$_2$) |
| | 12.9 ppm broad singlet (1H) (NH) |

The 2,6-difluorobenzaldehyde used as a starting compound can be prepared as described by A. M. Roe et al.: J.Med. Chem. 11 (1968) 814. b$_{21}$=88°–90° C.

EXAMPLE 9

2-(2,3-Difluorophenyl)-4,5-bis(4-methoxyphenyl)imidazole 200 ml of acetic acid, 77 g (1.0 mole) of ammonium acetate, 27 g (0.1 mole) of anisil and 14.95 g (0.105 mole) of 2,3-difluorobenzaldehyde are refluxed together for one hour. Boiling water is then added to the clear solution until a slight turbidity persists and the heating is stopped. After cooling the white precipitate formed is filtered off, washed with 2 N ammonia and then with water, dried and recrystallised from 2-propanol.

Yield of recrystallised products: 29.3 g (75%).

The product is homogenous by TLC and shows a melting point of 155.4°–158.5° C.

The IR-spectrum (KBr) shows the following characteristics: 3460 cm$^{-1}$ (broad) NH; 3140–2900 cm$^{-1}$ CH (aromatic); 2850 cm$^{-1}$ CH (OCH$_3$); 1625, 1525 and 1495 cm$^{-1}$ aromatic ring systems; 1240 cm$^{-1}$ (assym.) and 1040 cm$^{-1}$ (sym.) C-O-C; 840 cm$^{-1}$ 1,4-disubstituted benzene rings.

The 60 MHz $^1$H NMR-spectrum of a 10% solution in DMSO-d$_6$ shows the following characteristics:

| δ(ppm) = | 3.80 singlet (6H) (CH$_3$O) × 2 |
|---|---|
| | 7.0; 7.5 AB quartet (8H) (C$_6$H$_4$OCH$_3$) × 2 |
| | ~7.3 multiplet (2H) ⎫ |
| | ⎬ (C$_6$H$_3$F$_2$) |
| | 7.8 multiplet (1H) ⎭ |
| | 12.6 broad singlet (1H) (NH) |

The 2,3-difluorobenzaldehyde used as a starting compound can be prepared from 1,2-difluorobenzene in the same way as described for 2,6-difluorobenzaldehyde by A. M. Roe et al.: J.Med. Chem. 11 (1968) 814. b$_{15}$=60°–61° C.

EXAMPLE 10

2-(3,4-Difluorophenyl)-4,5-bis(4-methoxyphenyl)imidazole 200 ml of acetic acid, 77 g (1.0 mole) of ammonium acetate, 27 g (0.1 mole) of anisil and 14.95 g (0.105 mole) of 3,4-difluorobenzaldehyde are refluxed together for one hour. Boiling water is then added to the clear solution until a slight turbidity persists and the heating is stopped. After cooling the white precipitate formed is filtered off, washed with 2 N ammonia and then with water, dried and recrystallised from 2-propanol.

Yield of recrystallised product: 29.7 g (76%).

The product is homogenous by TLC and shows a melting point of 188°–191.1° C.

The IR-spectrum (KBr) shows the following characteristics: 3450 cm$^{-1}$ (broad) NH; 3100–2900 cm$^{-1}$ CH (aromatic); 2850 cm$^{-1}$ CH (OCH$_3$); 1620, 1530 and 1510 cm$^{-1}$ aromatic ring systems; 1255 cm$^{-1}$ (assym.) and 1040 cm$^{-}$(sym.) C-O-C; 840 cm$^{-1}$ 1,4-disubstituted benzene rings.

The 60 MHz $^1$H NMR-spectrum of a 10% solution in DMSO-d$_6$ shows the following characteristics:

| | |
|---|---|
| δ(ppm) = 3.93 | singlet (6H) (CH$_3$O) × 2 |
| 7.7; 7.1 | AB quartet (8H) (C$_6$H$_4$OCH$_3$) × 2 |
| 7.3 | multiplet (2H) ⎫ |
| 7.9–8.7 | multiplet (1H) ⎬ (C$_6$H$_3$F$_2$) |
| 13.1 | broad singlet (1H) (NH) ⎭ |

The 3,4-difluorobenzaldehyde used as a starting compound can be prepared as follows: 1,2-difluorobenzene is brominated by a method analogous to the one described in Organic Synthesis Coll. Vol. I p. 123. from the resulting 3,4-difluorobromobenzene, 3,4-difluorophenylmagnesiumbromide is prepared in diethylether, and this Grignard reagent is added dropwise to a solution of N-methylformanilide in tetrahydrofuran. From the reaction mixture, 3,4-difluorobenzaldehyde is obtained. b$_{17}$=80°–82° C.

EXAMPLE 11

2-(3,5-Difluorophenyl)-4,5-bis(4-methoxyphenyl)imidazole 200 ml of acetic acid, 77 g (1.0 mole) of ammonium acetate, 27 g (0.1 mole) of anisil and 14.95 g (0.105 mole) of 3,5-difluorobenzaldehyde are refluxed together for one hour. Boiling water is then added to the clear solution until a slight turbidity persists and the heating is stopped. After cooling the white precipitate formed is filtered off, washed with 2 N ammonia and then with water, dried and recrystallised from 2-propanol.

Yield of recrystallised product: 22 g (56%).

The product is homogenous by TLC and shows a melting point of 234°–237° C.

The IR-spectrum (KBr) shows the following characteristics: 3450 cm$^{-1}$ (broad) NH; 3140–2900 cm$^{-1}$ CH (aromatic); 2850 cm$^{-1}$ CH (OCH$_3$); 1635, 1530, 1500 and 1460 cm$^{-1}$ aromatic ring systems; 1255 cm$^{-1}$ (assym.) and 1040 cm$^{-1}$ (sym.) C-O-C; 840 cm$^{-1}$ 1,4-disubstituted benzene rings.

The 60 MHz $^1$H NMR-spectrum of a 10% solution in DMSO-d$_6$ shows the following characteristics:

| | |
|---|---|
| δ(ppm) = 3.85 | singlet (6H) (CH$_3$O) × 2 |
| 7.1; 7.6 | AB quartet (8H) (C$_6$H$_4$OCH$_3$) × 2 |
| 7.3 | multiplet (1H) ⎫ |
| 7.9 | multiplet (2H) ⎬ (C$_6$H$_3$F$_2$) |
| ~13 | broad singlet (1H) (NH) ⎭ |

The 3,5-difluorobenzaledehyde used as a starting compound can be prepared as follows: 3,5-difluorophenylmagnesiumbromide can be prepared as described by A. Roe and W. F. Little: J.Org.Chem. 20 (1955) 1577. A solution of 3,5-difluorophenylmagnesiumbromide in diethylether is added dropwise to a solution of N-methylformanilide in tetrahydrofuran. By working up this reaction mixture, 3,5-difluorobenzaldehyde is obtained. b$_{55}$=86°–88° C.

We claim:
1. The chemical compound 2-(2,4-difluorophenyl)-4,5-bis(4-methoxyphenyl)imidazole.
2. An analgesic composition which comprises an analgesic effective amount of the compound 2-(2,4-difluorophenyl)-4,5-bis(4-methoxyphenyl)imidazole and a pharmaceutically acceptable carrier.

* * * * *